United States Patent
Li et al.

(10) Patent No.: US 10,875,874 B2
(45) Date of Patent: Dec. 29, 2020

(54) GINKGOLIDE B DERIVATIVE AND PREPARATION METHOD AND USE THEREOF

(71) Applicant: Chengdu Baiyu Ginkgolide Pharmaceuticals Co., Ltd., Sichuan (CN)

(72) Inventors: Daxiong Li, Sichuan (CN); Huiqin Li, Sichuan (CN); Hong Ke, Sichuan (CN); Xiaobo Fan, Sichuan (CN); Yi Sun, Sichuan (CN)

(73) Assignee: Chengdu Baiyu Ginkgolide Pharmaceuticals Co. Ltd., Sichuan (CN)

( * ) Notice: Subject to any disclaimer, the term of this patent is extended or adjusted under 35 U.S.C. 154(b) by 13 days.

(21) Appl. No.: 16/063,615

(22) PCT Filed: Dec. 19, 2016

(86) PCT No.: PCT/CN2016/110802
§ 371 (c)(1),
(2) Date: Nov. 14, 2018

(87) PCT Pub. No.: WO2017/101881
PCT Pub. Date: Jun. 22, 2017

(65) Prior Publication Data
US 2019/0077811 A1    Mar. 14, 2019

(30) Foreign Application Priority Data
Dec. 18, 2015 (CN) .......................... 2015 1 0961751

(51) Int. Cl.
| C07D 493/00 | (2006.01) |
| C07D 493/22 | (2006.01) |
| A61K 31/365 | (2006.01) |
| A61P 9/12   | (2006.01) |
| C07D 519/00 | (2006.01) |

(52) U.S. Cl.
CPC .......... C07D 493/22 (2013.01); A61K 31/365 (2013.01); A61P 9/12 (2018.01); C07D 519/00 (2013.01)

(58) Field of Classification Search
CPC .................................................. C07D 493/00
See application file for complete search history.

(56) References Cited

U.S. PATENT DOCUMENTS

| 5,241,084 A | 8/1993 | Teng |
| 5,541,183 A | 7/1996 | Park et al. |
| 2003/0194370 A1 | 10/2003 | Stromgaard et al. |
| 2007/0098632 A1 | 5/2007 | Stromgaard et al. |

FOREIGN PATENT DOCUMENTS

| CN | 1139435 A | 1/1997 |
| CN | 1837212 A | 9/2006 |
| CN | 101880286 A | 11/2010 |
| CN | 103242337 A | 8/2013 |
| CN | 103508981 A | 1/2014 |
| CN | 104098584 A | 10/2014 |
| CN | 201510961751.4 | 12/2015 |
| CN | 105367582 A | 3/2016 |
| GB | 2211841 A | 7/1989 |
| KR | 10-0136986 B | 4/1998 |
| WO | WO 93/06107 | 4/1993 |
| WO | WO 9518131 A1 | 7/1995 |
| WO | WO 03/082185 | 10/2003 |
| WO | WO-03082185 A2 * | 10/2003 ........... C07D 493/20 |
| WO | WO2003082185 A2 * | 10/2003 |

OTHER PUBLICATIONS

Hui, A., et al. "Novel ginkgolide B derivative attenuated the function and expression of P-glycoprotein at the blood-brain barrier, presenting brain-targeting ability." Royal Society of Chemistry. (2016), vol. 6, pp. 31101-31106. (Year: 2016).*
Wu, Z. et al., Brain-Targeting Research of 10-O-Nicotinate Ginkgolide B: A New Prodrug of Ginkgolide B, Med. Chem. Res. (2012) 21:4028-4036.
International Search Report and Written Opinion for PCT/CN2016/110802 dated Jun. 22, 2017.
First Office Action from the State Intellectual Property Office of People's Republic of China for 201611177538.5.
PCT/CN2016/110802, Dec. 19, 2016, WO 2017/101881.
Jaracz et al., "Ginkolides: Selective Acetylations, Translactonization, and Biological Evaluation", Journal of Organic Chemistry, vol. 67, pp. 4623-4626. 2002.
Stromgaard et al., "Ginkolide Derivatives for Photolabeling Studies: Preparation and Pharmacological Evaluation", Journal of Medicinal Chemistry, vol. 45, pp. 4038-4046. 2002.
International Search Report and Written Opinion issued in PCT/CN2016/110802 dated Mar. 22, 2017, with English translation.
Third Office Action issued in CN 201611177538.5 dated Jul. 15, 2019, with English translation.
Notice of Reasons for Refusal issued in JP 2018-550641 dated Jul. 19, 2019, with English translation.
Zhu et al., "QSAR Analyses on Ginkgolides and Their Analogues Using CoMFA, CoMSIA, and HQSAR", Bioorganic & Medicinal Chemistry, Pergamon, GB, vol. 13, No. 2, Jan. 17, 2005.
Ze-Yu et al., "Brain-Targeting Research of 10—Nicotinate Ginkgolide B: a New Prodrug of Ginkgolide B", Medicinal Chemistry Research, Birkhauser-Verlag, Boston, vol. 21, No. 12, Dec. 24, 2011.
Chinese Office Action with English translation and complementary search for Chinese Application No. 201611177538 dated Feb. 20, 2019.

(Continued)

*Primary Examiner* — John S Kenyon
(74) *Attorney, Agent, or Firm* — McCarter & English, LLP

(57) ABSTRACT

Disclosed are a compound as shown in formula I or formula II or a pharmaceutically acceptable salt thereof, wherein $R_1$ is selected from pyrazinyl or substituted pyrazinyl; and $R_2$ is selected from pyrazinyl or substituted pyrazinyl, phenyl or substituted phenyl, alkyl or substituted alkyl.

4 Claims, No Drawings

(56) References Cited

OTHER PUBLICATIONS

Canadian Office Action for Canadian Application 3,008,698 dated Jun. 13, 2019.
Extended European Search Report for European Application No. 16874938 dated Jun. 14, 2019.
Supplementary European Search Report dated Oct. 1, 2019, for European Patent Application No. 16874938.
Korean Office Action with English translation dated Oct. 28, 2019, for Korean Patent Application No. 10-2018-7020564.

* cited by examiner

GINKGOLIDE B DERIVATIVE AND PREPARATION METHOD AND USE THEREOF

CROSS-REFERENCE TO RELATED APPLICATIONS

This application is a 35 U.S.C. § 371 National Stage filing of International Application No. PCT/CN2016/110802, filed on Dec. 16, 2016, which claims priority to Chinese Patent Application No. 201510961751.4 filed Dec. 18, 2015.

TECHNICAL FIELD

The present invention relates to a ginkgolide B derivative and a preparation method and use thereof.

BACKGROUND

The ginkgolide B (Ginkgolide B, GB) is one of main active ingredients extracted from ginkgo leaves, is the most powerful platelet activation factor (PAF) antagonist discovered so far, can be used for inhibiting platelet aggregation, resisting inflammations, resisting shock, protecting heart and cerebral vessels, treating acute pancreatitis and so on and is an effective drug for treating acute and chronic cerebral ischemic diseases. But the ginkgolide B is a diterpene compound with a six-membered ring cage-shaped structure, has a rigid structure and is poor in water solubility and low in bioavailability, thus, the full play of drug efficacy is limited, and the effect of clinical application of the ginkgolide B is affected.

In recent years, researches on structure modification of the ginkgolide B become a hot topic. In a document WO9306107, for the purpose of separation and purification, the structure of the ginkgolide B is reformed, but the reforming is only restricted to molecular internal chiral change, the water solubility of the ginkgolide B is not improved, and the anti-PAF activity is considerably weakened. Structure modification on ginkgolide B is reported in a document CN1139435A, the water solubility and anti-PAF activity of part of derivatized compounds are improved, however, synthesis processes are harsh and complicated and are lower in yield, and great difficulty is brought for actual production operation. Structure modification on 10-O position of ginkgolide B is also reported in a patent CN1837212A, a series of carboxylic acid and nitrogen-containing derivatized compounds are obtained, however, whether the water solubility and drug effect activity are improved or not is lack of detection data. Therefore, it is necessary for us to further perform structure modification on lead compounds of the ginkgolide B on the basis of predecessor's researches to discover ginkgolide B candidate drugs with higher activity, better water solubility and novel structures and apply the drugs to the prevention and treatment of cardiovascular and cerebrovascular diseases.

SUMMARY

An object of the present invention is to provide a ginkgolide B derivative with a novel structure and a medicinal value and a preparation method and use thereof, and a pharmaceutical composition comprising the ginkgolide B derivative, and thus, more drug selecting ways are provided for preventing, treating, curing, and/or alleviating cardiovascular and cerebrovascular diseases.

A compound as shown in formula I or formula II or a pharmaceutically acceptable salt thereof provided by the present invention:

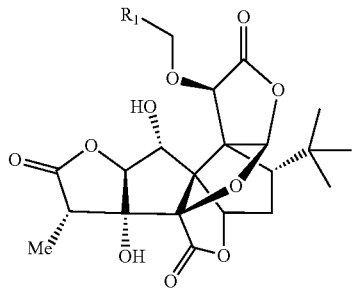

Formula I wherein $R_1$ is selected from pyrazinyl or substituted pyrazinyl;

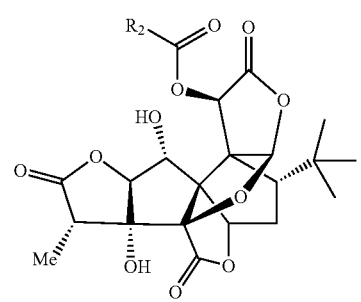

Formula II wherein $R_2$ is selected from pyrazinyl or substituted pyrazinyl, phenyl or substituted phenyl, alkyl or substituted alkyl.

Further, the compound is as shown in formula Ia:

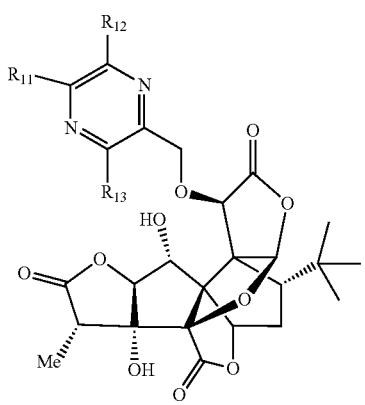

Formula Ia wherein $R_{11}$, $R_{12}$ and $R_{13}$ are separately or simultaneously selected from H, alkyl, substituted alkyl, ester group, alkoxy, halogen, hydroxyl, cyano, phenyl or substituted phenyl.

Further, in the compound as shown in the formula Ia, $R_{11}$, $R_{12}$ and $R_{13}$ are separately or simultaneously selected from $C_1$-$C_6$ alkyl or halogen substituted $C_1$-$C_6$ alkyl.

Further, the compound as shown in the formula Ia is:

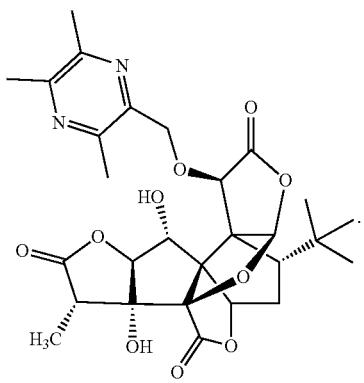

BM

Further, the compound is as shown in formula IIa, formula IIb or IIc:

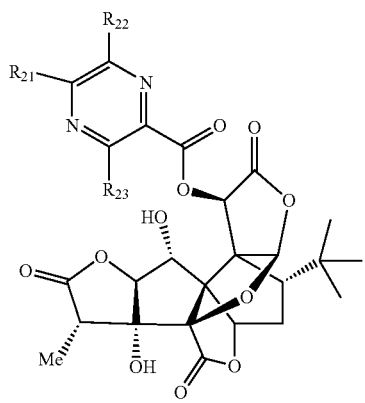

Formula IIa wherein $R_{21}$, $R_{22}$ and $R_{23}$ are separately or simultaneously selected from H, alkyl, substituted alkyl, ester group, alkoxy, halogen, hydroxyl, cyano, phenyl or substituted phenyl;

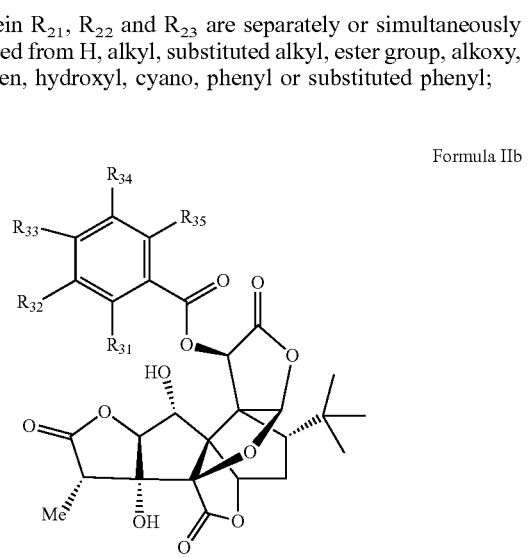

Formula IIb wherein $R_{31}$, $R_{32}$, $R_{33}$, $R_{34}$ and $R_{35}$ are separately or simultaneously selected from H, alkyl, substituted alkyl, ester group, alkoxy, halogen, hydroxyl, cyano, phenyl or substituted phenyl;

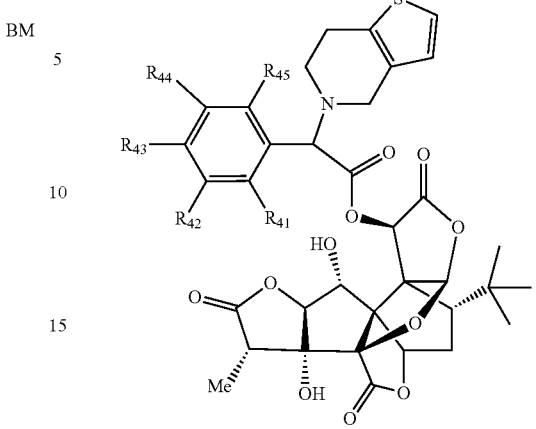

Formula IIc wherein $R_{41}$, $R_{42}$, $R_{43}$, $R_{44}$ and $R_{45}$ are separately or simultaneously selected from H, alkyl, substituted alkyl, ester group, alkoxy, halogen, hydroxyl, cyano, phenyl or substituted phenyl.

Further, in the compound as shown in the formula IIa, $R_{21}$, $R_{22}$ and $R_{23}$ are separately or simultaneously selected from $C_1$-$C_6$ alkyl or halogen substituted $C_1$-$C_6$ alkyl.

Further, the compound as shown in the formula IIa is:

BZ

Further, in the compound as shown in the formula IIb, $R_{31}$ is selected from ester group or ester group substituted alkyl, and $R_{32}$, $R_{33}$, $R_{34}$ and $R_{35}$ are H simultaneously.

Further, in the compound as shown in the formula IIb, $R_{31}$ is selected from $C_2$-$C_6$ ester group or ester group substituted alkyl as shown in formula A:

Formula A wherein $R_{311}$ and $R_{312}$ are separately or simultaneously selected from $C_2$-$C_6$ ester group or $C_1$-$C_6$ alkyl, and $R_{311}$ and $R_{312}$ are not $C_1$-$C_6$ alkyl simultaneously.

Further, the compound as shown in the formula IIb is:

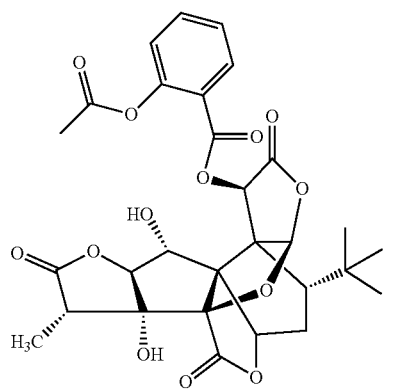
BA or

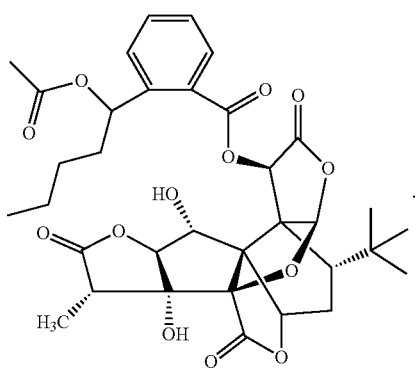
BD

Further, in the compound as shown in the formula IIc, $R_{41}$, $R_{42}$, $R_{43}$, $R_{44}$ and $R_{45}$ are separately or simultaneously selected from H or halogen.

Further, the compound as shown in the formula IIc is:

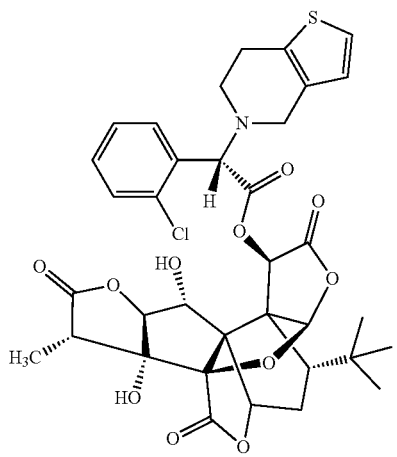
BL

Further, the pharmaceutically acceptable salt is selected from organic acid salts or inorganic acid salts.

Further, the organic acid salts are selected from methanesulfonate, p-toluene sulfonate, benzene sulfonate, lactate, zitrat(citrate), succinate, oxalate, malate, fumarate, maleate, tartrate, acetate, propionate or succinate; and the inorganic acid salts are selected from hydrochloride, sulfate, hydrobromide or phosphate.

The present invention further provides a preparation method of the compound as shown in formula Ia. The method comprises the following steps:

a. dissolving ginkgolide B in an organic solvent, adding

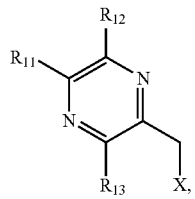

or

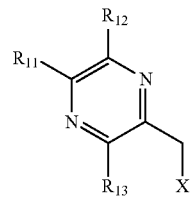

an inorganic base and a catalyst, and performing a reaction at a temperature of 50° C.-60° C. to obtain a reaction solution; wherein X is halogen; and b. separating and purifying the reaction solution obtained in the step a, thereby obtaining the compound as shown in the formula Ia.

Further, in the step a,
the ginkgolide B and

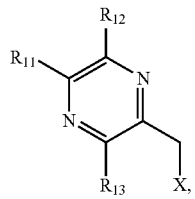

have a mole ratio of 1:1 to 1:5; and the ginkgolide B and the inorganic base have a mole ratio of 1:5 to 1:20;

preferably, the ginkgolide B and

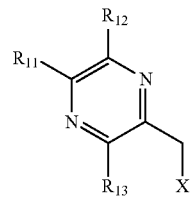

have the mole ratio of 1:2 to 1:3; and the ginkgolide B and the inorganic base have the mole ratio of 1:10 to 1:20.

Further, in the step a, the organic solvent is selected from acetonitrile or N, N-dimethylformamide; the inorganic base is selected from potassium carbonate, sodium carbonate or caesium carbonate; and the catalyst is potassium iodide.

The present invention further provides a preparation method of the compound as shown in formula IIa, formula IIb or formula IIc. The method comprises the following steps:

① dissolving the ginkgolide B and a compound as shown in formula V in an organic solvent, adding a catalyst and a condensing agent, performing a reaction for a period of 4 to 6 hours at a temperature of 20° C.-30° C. to obtain a reaction solution;

wherein the compound as shown in formula V for preparing the compound as shown in formula IIa is:

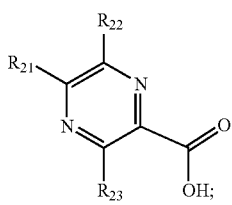

the compound as shown in formula V for preparing the compound as shown in formula IIb is:

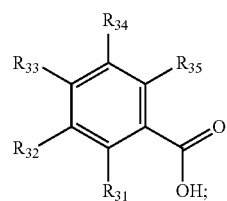

and
the compound as shown in formula V for preparing the compound as shown in formula IIc is:

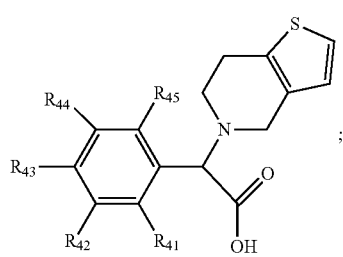

and
② separating and purifying the reaction solution obtained in the step ①, thereby obtaining the compound as shown in the formula IIa, formula IIb or formula IIc.

Further, in the step ①, the ginkgolide B and the compound as shown in the formula V have a mole ratio of 1:1 to 1:5; the ginkgolide B and the catalyst have a mole ratio of 1:0.1 to 1:0.3; and the ginkgolide B and the condensing agent have a mole ratio of 1:1.2 to 1:1.6.

Further, in the step ①, the organic solvent is selected from acetonitrile or N, N-dimethylformamide; the catalyst is selected from 4-dimethylaminopyridine or 1-hydroxylbenzotriazole; the condensing agent is selected from 1-(3-dimethylaminopropyl)-3-ethylcarbodiimide hydrochloride, dicyclohexyl carbodiimide or diisopropyl carbodiimide.

The present invention further provides a pharmaceutical composition, comprising the compound as shown in formula I or formula II or the pharmaceutically acceptable salt thereof as an active ingredient, and comprising pharmaceutically acceptable accessories or auxiliary ingredients.

The present invention further provides use of the compound as shown in formula I or formula II or pharmaceutically acceptable salt thereof in preparation of drugs for treating and/or preventing cardiovascular and cerebrovascular diseases.

Further, the cardiovascular and cerebrovascular diseases comprise hypertension, cerebral apoplexy, coronary diseases, arrhythmia, heart failure, dyslipidemia, pulmonary vascular diseases, chronic kidney diseases, peripheral vascular diseases, etc., such as myocardial infarction, coronary artery diseases, atherosclerosis, left main diseases, bifurcation lesions, angina pectoris, thrombosis, pulmonary heart diseases, endocrinopathy heart diseases, anemic heart diseases, cardiac neurosis, nutritional metabolic heart diseases, aortic aneurysm, lower extremity atherosclerotic diseases, peripheral arterial diseases, intracranial aneurysm, arteriosclerotic aneurysm, ischemic cerebral apoplexy, hemorrhagic cerebral apoplexy, hyperlipidemia, arteriosclerosis, sudden cardiac death, apoplexy, vascular thrombosis, pulmonary embolism, atrial fibrillation, myocardial diseases, pericardial diseases, valvular heart diseases, hypertensive encephalopathy, hypertension with cerebral stroke, cerebral hemorrhage, cerebral thrombosis, cerebral embolism, cerebral infarction, cerebral arteritis, cerebral arteriosclerosis, lacunar infarction, vascular dementia, chronic kidney diseases, chronic cardiac insufficiency, gouty nephropathy, diabetic nephropathy and/or abnormal renal function.

Further, the myocardial infarction is acute myocardial infarction; the coronary artery diseases are acute coronary artery syndromes or coronary artery vascular recanalization; the hypertension is primary hypertension; the apoplexy is cerebral apoplexy; the arrhythmia is ventricular arrhythmia, complex arrhythmia, inherited arrhythmia or malignant arrhythmia.

The compound as shown in formula I or formula II or the pharmaceutically acceptable salt thereof, provided by the present invention, particularly compounds BZ, BA, BL, BM, BD or salts thereof have a good drug effect on the prevention and/or treatment of hypertension, cerebral apoplexy, coronary diseases, arrhythmia, heart failure, dyslipidemia, pulmonary vascular diseases, chronic kidney diseases, peripheral vascular diseases, etc., such as myocardial infarction, coronary artery diseases, atherosclerosis, left main diseases, bifurcation lesions, angina pectoris, thrombosis, pulmonary heart diseases, endocrinopathy heart diseases, anemic heart diseases, cardiac neurosis, nutritional metabolic heart diseases, aortic aneurysm, lower extremity atherosclerotic diseases, peripheral arterial diseases, intracranial aneurysm, arteriosclerotic aneurysm, ischemic cerebral apoplexy, hemorrhagic cerebral apoplexy, hyperlipidemia, arteriosclerosis, sudden cardiac death, apoplexy, vascular thrombosis, pulmonary embolism, atrial fibrillation, hypertensive encephalopathy, hypertension with cerebral stroke, cerebral hemorrhage, cerebral thrombosis, cerebral embolism, cerebral infarction, cerebral arteritis, cerebral arteriosclerosis, lacunar infarction, vascular dementia, chronic kidney diseases, chronic cardiac insufficiency, gouty nephropathy, diabetic nephropathy and/or abnormal renal function, and thus, a new choice is provided for clinically preventing and/or treating the cardiovascular and cerebrovascular diseases.

With reference to definition of terms used in the present invention, unless otherwise mentioned, initial definitions of groups or terms provided by the present invention are applicable to the groups or terms in the entire description; and terms not specifically defined in the present invention should present meanings capable of being offered by those skilled in the art according to disclosed contents and the context.

'Substitution' means that hydrogen atoms in molecules are substituted by other different atoms or molecules.

A minimum value and a maximum value of the carbon atom content in carbon-hydrogen groups are represented by prefixes, for example, prefix $(C_a\text{-}C_b)$ alkyl groups show any alkyl containing a to b carbon atoms. Therefore, for example, $C_1$-$C_6$ alkyl is alkyl containing 1-6 carbon atoms.

The term 'pharmaceutically acceptable' means that some supports, carriers, diluents, accessories and/or formed salts are chemically or physically compatible with other ingredients for forming some medicine dosage forms generally and are physiologically compatible with receptors.

Terms 'salt' and 'medicinal salt' mean above-mentioned compounds or stereoisomers thereof and acidic and/or basic salts formed by inorganic and/or organic acids and bases, also comprise amphoteric ion salts (inner salts) and further comprise quaternary ammonium salts, for example alkyl ammonium salts. These salts may be directly obtained from the final separation and purification of compounds. These salts may also be obtained through mixing the compounds or stereoisomers thereof with a certain amount of acid or base properly (for example, equivalent). These salts may be collected through forming precipitates in solutions and filtering, or obtained through evaporating solvents and then recycling, or prepared through performing a reaction in aqueous media and then performing freeze drying. In the present invention, the salts may be hydrochloride, sulfate, citrate, methanesulfonate, benzene sulfonate, lactate, p-toluene sulfonate, hydrobromide, hydrofluoride, phosphate, acetate, propionate, succinate, oxalate, malate, succinate, fumarate, maleate, tartrate, trifluoroacetate or salicylate of the compounds.

Apparently, other modifications, substitutions or alterations of multiple forms may be made on the premise of not departing from the above-mentioned fundamental technical thought of the present invention according to the above-mentioned contents of the present invention in accordance with ordinary technical knowledge and habitual means in the art.

The above-mentioned contents of the present invention are further described in detail below with reference to specific embodiments in the form of embodiments. However, it should not be understood that the range of the subject of the present invention is only limited to the following embodiments. All technologies achieved on the basis of the above-mentioned contents of the present invention belong to the scope of the present invention.

DETAILED DESCRIPTION

Raw materials and equipment used in specific embodiments of the present invention are all known products and are purchased from commercially available products.

1. Acetylsalicylic acid: Chengdu Kelong Chemical Reagent Factory, LN 2013101601

2. Preparation of 3,5,6-trimethylpyrazine-2-formic Acid 10 g (73.42 mmol) of tetramethyl pyrazine is weighed and added into a 250 ml three-necked bottle, 100 ml of water is added into the three-necked bottle, heating is carried out to 35-40° C., 11.6 g of $KMnO_4$ is added into the three-necked bottle with stirring, and a reaction is carried out for a period of 10 h while the temperature is preserved. Extraction with ethyl acetate is carried out, drying is carried out, and then, a solvent is removed to obtain 6.2 g of light-yellow solid, wherein the yield is 50.82%.

3. Preparation of S(+)-2-(2-chlorophenyl)-2-(4,5,6, 7-tetrahydrothieno[3,2-c]pyridin-5)acetic acid 20 g of clopidogrel is weighed and added into a 500 ml three-necked bottle, 150 ml of methanol and 100 ml of 2 mol/L sodium hydroxide are added into the three-necked bottle, dissolving is carried out under stirring, then, heating is performed to 50° C., a reaction is carried out for a period of 1 h, depressurizing is performed to remove the methanol, then, 100 ml of water is added to dilute, cooling is performed to 0-10° C., the pH is adjusted to be acidic with hydrochloric acid, then, 150 ml of ethyl acetate is added, extracting and drying are performed, and then, the solvent is removed to obtain 13.2 g of off-white solid, wherein the yield is 69%.

4. Preparation of 2-bromomethyl-3,5,6-trimethylpyrazine

Ligustrazine (20.0 g, 0.147 mol), NBS (26.8 g, 0.151 mol), a catalyst benzoyl peroxide (0.058 g, 0.232 mmol) and a solvent $CCl_4$ (75.0 mL) are sequentially added into a 250 ml three-necked bottle, irradiating with an incandescent lamp is performed, heating is performed to 75° C. in an oil bath, and a reaction is performed for a period of 10 hours. Filtering is performed to remove the solvent from filter liquor to obtain a concentrate. Purification is performed by column chromatography to obtain 15.8 g of light-yellow solid, i.e., 2-bromomethyl-3,5,6-trimethylpyrazine, wherein the yield is 50%.

5. Preparation of 2-(1-acetoxylamyl)benzoic Acid 12.4 g (65 mmol) of butylphthalide is dissolved in a 500 mL single-necked flask containing 100 mL of methanol, 100 mL of 2 mol/L NaOH solution is added, stirring is performed for a period of 1 h at a temperature of 50° C., reduced pressure distillation is performed to remove the methanol, then, 100 mL of distilled water is added to dilute, cooling is performed to −5° C., the pH is adjusted to be 2 to 3 with 5% hydrochloric acid with stirring, extraction is performed with ethyl ether, drying is performed, and then, the ethyl ether is removed at a low temperature to obtain a white solid. 20 mL of triethylamine, 2.5 g of DMAP and 200 mL of dichloromethane are separately added into the white solid in a 500 mL three-necked bottle, stirring is performed to dissolve at a temperature of −10° C. to 0° C., then, 11 mL of acetyl chloride is dropwise added, and stirring is performed for a period of 5 h while preserving the temperature. 100 mL of water is added, stirring is performed for a period of 0.5 h at room temperature, an organic layer is separated out, drying is performed, then, the solvent is removed, and purifying is performed to obtain 6.35 g of white solid, wherein the yield is 38.96%.

Similarly, 3,5,6-trimethylpyrazine-2-formic acid, 2-bromomethyl-3,5,6-trimethylpyrazine and 2-(1-acetoxylamyl) benzoic acid all can be purchased from the market.

Embodiment 1: Preparation of Compound BZ

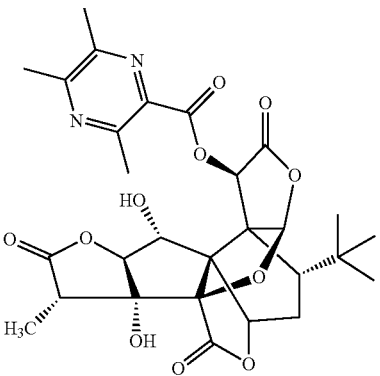

5.0 g (11.78 mmol) of GB and 2.55 g (15.32 mmol) of 3,5,6-trimethylpyrazine-2-formic acid are weighed and dissolved in acetonitrile, and stirring and mixing are performed in an ice bath. Then, 0.29 g (2.36 mmol) of 4-dimethylaminopyridine (DMAP) and 3.17 g (16.49 mmol) of 1-(3-dimethylaminopropyl)-3-ethylcarbodiimide hydrochloride (EDC.HCl) are added, stirring is performed for a period of 1 hour in the ice bath, then, the mixture is subjected to a reaction for a period of 6 h at a temperature of 20° C., rotary evaporation is performed to remove the solvent, a coarse product is dissolved with ethyl acetate, the product is washed twice with 5% NaHCO$_3$, and then the product is washed once with a saturated sodium chloride solution. An organic phase is collected, drying, filtering and concentrating are performed, and separating and purifying are performed to obtain 2.80 g of white solid BZ in all, wherein the yield is 41.48%, and the HPLC purity is 99.80%.

LC-MS: 573.2[M+H$^+$], 595.2[M+Na$^+$].

$^1$H-NMR (DMSO, 400 MHz): 1.02 (s, 9H, t-Bu), 1.13-1.19 (d, 3H, 14-Me), 1.75-1.79 (dd, 1H, 8-H), 1.84-1.89 (d, 1H, 7α-H), 2.16-2.21 (q, 1H; 7β-H), 2.49-2.58 (dd, 6H, 2CH$_3$-pyrazine), 2.76 (s, 3H, CH$_3$-pyrazine), 2.86-2.91 (q, 1H, 14-H), 4.15-4.18 (q, 1H, 1-H), 4.72-4.74 (d, 1H, 2-H), 5.46-5.47 (d, 1H, 1-OH), 6.33 (s, 1H, 10-H), 6.50 (s, 1H, 6-H), 6.57 (s, 1H, 12-H), 6.89-6.90 (d, 1H, 3-OH).

Embodiment 2: Preparation of Compound BA

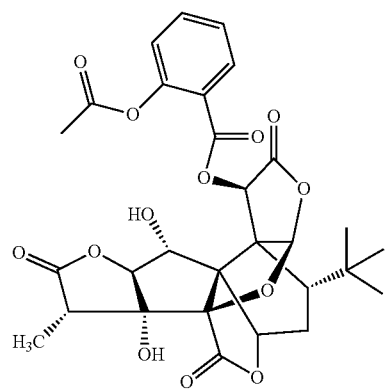

5.0 g (11.78 mmol) of GB and 2.76 g (15.32 mmol) of acetylsalicylic acid are weighed and dissolved in acetonitrile, and stirring and mixing are performed in an ice bath. Then, 0.29 g (2.36 mmol) of 4-dimethylaminopyridine (DMAP) and 3.17 g (16.49 mmol) of 1-(3-dimethylaminopropyl)-3-ethylcarbodiimide hydrochloride (EDC.HCl) are added, stirring is performed for a period of 1 hour in the ice bath, then, the mixture is subjected to a reaction for a period of 4 h at a temperature of 30° C., rotary evaporation is performed to remove the solvent, a coarse product is dissolved with ethyl acetate, the product is washed twice with 5% NaHCO$_3$, and then the product is washed once with saturated sodium chloride. An organic phase is collected, drying, filtering and concentrating are performed, and separating and purifying are performed to obtain 2.52 g of white solid BA in all, wherein the yield is 36.52%, and the HPLC purity is 99.13%.

MS: 609.16[M+Na$^+$], C$_{29}$H$_{30}$NaO$_{13}$.

$^1$H-NMR (CDCl$_3$, 400 MHz): 1.08 (s, 9H, t-Bu), 1.24-1.26 (d, 3H, 14-Me), 1.99-2.03 (dd, 1H, 8-H), 2.16 (s, 3H, —CH$_3$CO—), 2.24 (d, 1H, 7α-H), 2.30-2.37 (q, 1H, 7β-H), 3.01-3.09 (q, 1H, 14-H), 4.08-4.13 (q, 1H, 1-H), 4.20-4.22 (d, 1H, 2-H), 4.63-4.67 (d, 1H, 1-OH), 5.64-5.65 (s, 1H, 10-H), 6.14 (s, 1H, 6-H), 6.21 (s, 1H, 12-H), 6.91-7.99 (ddd, 4H, Ar), 10.03 (s, 1H, 3-OH).

Embodiment 3: Preparation of Compound BL

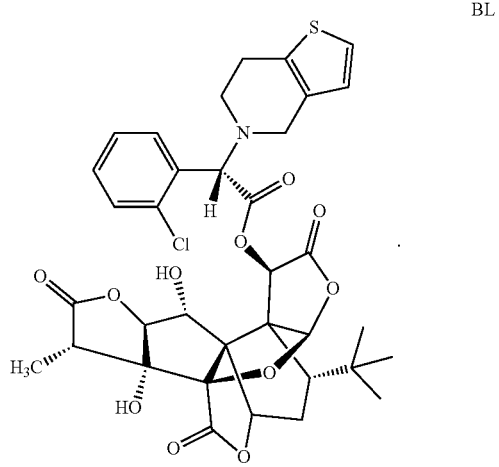

5.0 g (11.78 mmol) of GB and 4.70 g (15.32 mmol) of S(+)-2-(2-chlorophenyl)-2-(4,5,6,7-tetrahydrothieno[3,2-c]pyridin-5)acetic acid are weighed and dissolved in acetonitrile, and stirring and mixing are performed in an ice bath. Then, 0.29 g (2.36 mmol) of 4-dimethylaminopyridine (DMAP) and 3.17 g (16.49 mmol) of 1-(3-dimethylaminopropyl)-3-ethylcarbodiimide hydrochloride (EDC.HCl) are added, stirring is performed for a period of 1 hour in the ice bath, and then, the mixture is subjected to a reaction for a period of 5 h at a temperature of 25° C. Rotary evaporation is performed to remove the solvent, a coarse product is dissolved with ethyl acetate, the product is washed twice with 5% NaHCO$_3$, and then the product is washed once with saturated sodium chloride. An organic phase is collected, drying, filtering and concentrating are performed, and separating and purifying are performed to obtain 3.46 g of white solid BL in all, wherein the yield is 41.09%, and the HPLC purity is 99.58%.

LC-MS: 714.3[M+H$^+$], 736.0[M+Na$^+$].

$^1$H-NMR (CDCl$_3$, 400 MHz): 1.05 (s, 9H, t-Bu), 1.25-1.36 (d, 3H, 14-Me), 1.78-1.83 (dd, 1H, 8-H), 2.00-2.04 (m, 4H, —CH$_2$CH$_2$—), 2.28-2.35 (d, 1H, 7α-H), 2.82 (q, 1H, 7β-H), 2.94-3.01 (q, 1H, 14-H), 3.86-3.87 (d, 2H, —CH$_2$—), 4.09 (s, 1H, —CHCO—), 4.11-4.14 (q, 1H, 1-H), 4.17-4.18 (d, 1H, 2-H), 4.51-4.53 (d, 1H, 1-OH), 5.41-5.43 (s, 1H, 10-H), 5.43-5.45 (d, 1H, 6-H), 6.08 (s, 1H, 12-H), 6.23 (s, 1H, 3-OH), 6.67-6.69 (dd, 1H, —CHS—), 7.15-7.18 (dd, 1H, —CHCHS—), 7.36-7.68 (m, 4H, Ar).

Embodiment 4: Preparation of Compound BM

BM

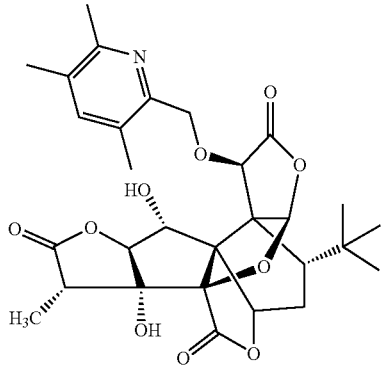

2.0 g of ginkgolide B is dissolved in 50 ml of acetonitrile, 0.96 g of 2-bromomethyl-3,5,6-trimethylpyrazine (1.2 eq), 6.81 g of potassium carbonate (10 eq) and a small amount of KI catalyst are sequentially added, and a reaction is performed at a temperature of 60° C. until the raw material ginkgolide B reacts completely. Cooling is performed to room temperature, filtering is performed, and then, filter liquor is subjected to rotary evaporation to obtain a light-yellow oily matter. Column-chromatography purification (V petroleum ether:V ethyl acetate=2:1) is performed to obtain 1.05 g of white solid, i.e., BM, wherein the yield is 39.92%, and the HPLC purity is 98.25%.

LC-MS: 559.3[M+H$^+$], 581.3[M+Na$^+$].

$^1$H-NMR (DMSO, 400 MHz): 1.14 (s, 9H, t-Bu), 1.16-1.20 (d, 3H, 14-Me), 1.80-1.85 (dd, 2H, 7-H), 2.15-2.8 (t, 1H, 8-H), 2.42 (s, 3H, —CH$_3$), 2.49-2.53 (d, 6H, —CH$_3$), 2.82-2.88 (q, 1H, 14-H), 4.17-4.19 (d, 1H, 1-H), 4.71-4.73 (d, 1H, 2-H), 4.94-4.98 (d, 1H, 1-OH), 5.41 (s, 1H, —CH$_2$—), 5.42 (s, 1H, 10-H), 5.43-5.45 (d, 1H, 6-H), 5.54 (s, 1H, 12-H), 6.23 (s, 1H, 3-OH).

Embodiment 5: Preparation of Compound BD

BD

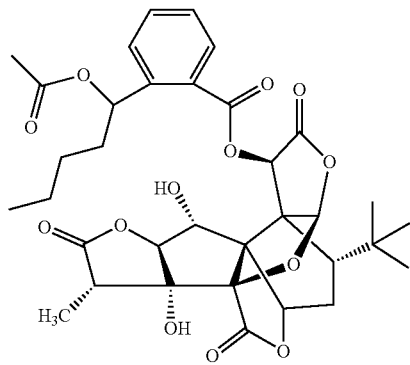

5.0 g (11.78 mmol) of GB and 3.83 g (15.32 mmol) of 2-(1-acetoxylamyl)benzoic acid are weighed and dissolved in acetonitrile, and stirring and mixing are performed in an ice bath. Then, 0.29 g (2.36 mmol) of 4-dimethylaminopyridine (DMAP) and 3.17 g (16.49 mmol) of 1-(3-dimethylaminopropyl)-3-ethylcarbodiimide hydrochloride (ED-C.HCl) are added, stirring is performed for a period of 1 hour in the ice bath, then, the mixture is subjected to a reaction for a period of 5 h at a temperature of 25° C., rotary evaporation is performed to remove the solvent, a coarse product is dissolved with ethyl acetate, the product is washed twice with 5% NaHCO$_3$, and then the product is washed once with saturated sodium chloride. An organic phase is collected, drying, filtering and concentrating are performed, and separating and purifying are performed to obtain 2.90 g of white solid BD in all, wherein the yield is 37.46%, and the HPLC purity is 98.14%.

LC-MS: 679.2[M+Na$^+$].

$^1$H-NMR (CDCl$_3$, 400 MHz): 0.87-0.91 (t, 3H, —CH$_3$), 1.12 (s, 9H, t-Bu), 1.27-1.29 (d, 3H, 14-Me), 1.32-1.36 (dd, 2H, 7-H), 1.45-1.49 (t, 1H, 8-H), 1.75-1.92 (m, 4H, —CH$_2$CH$_2$—), 1.98 (s, 5H, —COCH$_3$, —CH$_2$CH$_3$), 2.37-2.39 (q, 1H, 14-H), 3.03-3.09 (q, 2H, 1-H, 2-H), 4.37-4.39 (d, 1H, 1-OH), 4.54-4.56 (d, 1H, 10-H), 5.50-5.51 (d, 1H, 6-H), 5.89-5.94 (m, 1H, —CHCH$_2$—), 6.13 (s, 1H, 12-H), 6.23 (s, 1H, 3-OH), 7.32-7.38 (m, 2H, ArH), 7.46-7.48 (d, 1H, ArH), 7.50-7.54 (d, 1H, ArH).

Embodiment 6: Preparation of BZ Methanesulfonate 2.0 g of BZ is added into 50 mL of acetone, heating is performed to a temperature of 40-50° C. with stirring, 0.44 g of methanesulfonic acid is slowly dropwise added into a solution after the solution is clarified, the solution is cooled after dropwise adding is completed, stirring is performed for a period of 30 min, and filtering and drying are performed to obtain 1.85 g of BZ methanesulfonate, wherein the yield is 79.06%.

Embodiment 7: Preparation of BM Methanesulfonate 0.9 g of BM is added into 30 mL of acetone, heating is performed to a temperature of 40-50° C. with stirring, 0.19 g of methanesulfonic acid is slowly dropwise added into a solution after the solution is clarified, the solution is cooled after dropwise adding is completed, stirring is performed for a period of 30 min, and filtering and drying are performed to obtain 0.82 g of BM methanesulfonate, wherein the yield is 81.56%.

Embodiment 8: Preparation of BZ Hydrochloride 1.0 g of BZ is added into 30 mL of anhydrous ethyl alcohol, heating is performed to a temperature of 60-70° C. with stirring, an ethanol solution of hydrogen chloride (with the content of 30-40%) is slowly dropwise added into a solution after the solution is clarified until the pH of the solution is about 3, cooling is performed after the dropwise adding is completed, the material is allowed to stand to crystallize so as to separate out a white solid, filtering is performed, and then drying is performed to obtain 0.72 g of BZ hydrochloride, wherein the yield is 67.92%.

Embodiment 9: Preparation of BM Hydrochloride 1.5 g of BM is added into 50 mL of anhydrous ethyl alcohol, heating is performed to a temperature of 60-70° C.

with stirring, an ethanol solution of hydrogen chloride (with the content of 30-40%) is slowly dropwise added into a solution after the solution is clarified until the pH of the solution is about 3, cooling is performed after the dropwise adding is completed, the material is allowed to stand to crystallize so as to separate out a white solid, filtering is performed, and then drying is performed to obtain 0.95 g of BM hydrochloride, wherein the yield is 59.38%.

Beneficial effects of the present invention are described below in a test example manner.

Text Example 1: Water Solubility Test

Measuring method: samples are ground to obtain fine powder, target compounds are quantitatively weighed, the weighed compounds are added into purified water, and the solubility of the compounds is investigated by ultrasonics. A result is as shown in a table 1.

TABLE 1

Solubility of each target compound in water

| Compound | Solubility in water (mg/mL) |
| --- | --- |
| Ginkgolide B (GB) | 0.11 |
| BM | 0.25 |
| BM methanesulfonate | 4.20 |
| BM hydrochloride | 4.65 |
| BZ | 0.30 |
| BZ methanesulfonate | 5.02 |
| BZ hydrochloride | 5.10 |
| BA | 0.22 |
| BL | 0.20 |
| BD | 0.25 |

The result shows that water solubility of ginkgolide B derivatives and salts thereof is obviously improved compared with that of ginkgolide B.

Text Example 2: Pharmacological Test of Ginkgolide B Derivatives on Pressure Lowering of Primary Hypertension The primary hypertension is a genetic heterogeneity disease, and the hypertension is generated by a plurality of genes with weak effects through joint action and is affected by a series of environmental factors. A pathologic process of the hypertension often relates to artery blood vessel wall thickening, myocardial fibrosis, left ventricular hypertrophy and nephro-angiosclerosis, the injury to hypertension target organs is caused, the incidence rate and death rate of cardiovascular and cerebrovascular incidents and nephropathy are obviously increased, and thus, the hypertension is extremely dangerous to human Therefore, reasonable control of blood pressure has a very important clinical significance.

Spontaneously hypertensive rats (SHR) have many similarities with human primary hypertension, including hereditary character, pathogenesis process, occurrence of hypertension complication, and thus, the SHR rats are reputed as optimal animal models for researching the human primary hypertension and have been extensively applied to experimental researches on hypertension pathogenesis and curative effect of anti-hypertension drugs. Therefore, the SHR rats are selected as test animals in the test.

1. Test Materials 1.1 Test drugs: BZ, BA, BL, BM, BD and GB, purity>98%.

1.2 Positive control drug: Captopril Tablets, 25 mg/tablet, Shanghai pukang pharmaceutical Co., Ltd., Lot Number: 101003.

1.3 Test instruments: BP-6 non-invasive animal blood pressure measuring system (Chengdu Taimeng Technology Co., Ltd.); FA1004 electronic analytical balance (Shanghai Precision Scientific Instrument Co., Ltd.).

1.4 Test animals: 112 SHR rats with the age of 14 weeks, wherein the female and male SHR rats are half and half, have the body weight of (200-250) g and are provided by Beijing Vital River Laboratory Animal Technology Co., Ltd., and a laboratory animal production license number is SCXK (Beijing) 2007-001; 8 healthy Wistar rats with the same weeks of age, wherein the female and male Wistar rats are half and half, have the body weight of (200-250) g and are provided by animal center of Nanjing medical college, and a laboratory animal production license number is SCXK (Suzhou) 2008-0004.

2. Test Method 2.1 Grouping and administration of animals: 112 SHR rats (the female and male SHR rats are half and half, and the female rats are not pregnant) with the body weight of 200-250 g are taken, the rats are enabled to adapt to a laboratory for a period of 5 d, blood pressure is measured once at a day to enable the rats to adapt to the environment and detect stimulation. Then, weighing and numbering are carried out, and the SHR rats are equally divided into 14 groups randomly (each group comprises 8 rats), i.e., an SHR rat model control group, a positive control group (captopril, 27 mg/kg), a BZ large-dose group (120 mg/kg/d), a BZ small-dose group (60 mg/kg/d), a BA large-dose group (120 mg/kg/d), a BA small-dose group (60 mg/kg/d), a BL large-dose group (120 mg/kg/d), a BL small-dose group (60 mg/kg/d), a BM large-dose group (120 mg/kg/d), a BM small-dose group (60 mg/kg/d), a BD large-dose group (120 mg/kg/d), a BD small-dose group (60 mg/kg/d), a GB large-dose group (120 mg/kg/d) and a GB small-dose group (60 mg/kg/d). In addition, 8 healthy Wistar rats are taken as a normal control group. Intragastric administration is performed on the rats of each drug group separately according to the above-mentioned doses by 1 mL/100 g body weight, intragastric administration is performed on the rats of the normal control group and the rats of the SHR rat model control group with an equal volume of distilled water, and administration is performed continuously for 8 weeks.

2.2 General state: during observation, conditions such as mind, water drinking, food intake, bowel movement, hair color, body weight and range of motion of rats are observed. Irritable degrees of the rats are divided into III levels: a level I means that the rats are free of obvious response when necks of the rats are seized; a level II means that the rats scream and startle when the necks of the rats are seized; and a level III means that the rats bite or rats of same cages frequently fight when the necks of the rats are seized.

2.3 Blood pressure measuring: caudal artery systolic pressure of rats is measured with a Bp-6 noninvasive blood pressure measuring system. Under the condition that the rats are calm, the systolic pressure is continuously measured for 3 times, and the average value of the measured systolic pressure is taken as a pressure measuring result. Observation indexes: ① single-administration pressure lowering effect: blood pressure of the rats is measured before administration and blood pressure conditions are measured 30 min, 60 min, 90 min and 120 min after first administration; and ② continuous-administration pressure lowering condition: blood pressure is separately measured 30 min after administration at 1 d, 7 d, 13 d, 19 d, 25 d, 35 d, 49 d and 56 d, the blood pressure is repeatedly measured for 3 times at a day, and the average value of obtained values is taken as a final blood pressure value.

2.4 Data statistical method: a test data result is represented by mean±standard deviation (x±s), one-factor variance analysis check is carried out by adopting a software SPSS15, and $P<0.05$ shows that the difference has a remarkable statistics significance.

3 Test Result 3.1 Influence on general state of spontaneously hypertensive rats: the rats of the normal control group are normal in food intake, drinking and motion conditions, sensitive in response, healthy and glossy in hair color, good in mental state and free of any unusual response; the rats of the SHR model group gradually present that back hair is fluffy, clustered and dim, the appetite is reduced, the body weight is reduced, the mind is dispirited and irritable, and the rats are prone to the behaviors of intense resisting, attacking and so on during administration and blood pressure detection, and irritable degrees are mostly changed to a level II and a level III from a level I; and after single administration of ginkgolide B and derivatives thereof, behavioral general state observations of rats of each group are free of obvious difference from those of the model control group. After 2 weeks of continuous-administration treatment, mental states are obviously changed for the better, emotions are relatively stable, the food intake is obviously increased, and the body weight is increased faster. The food intake and body weight of rats of each group are weighed once per week, the food intake of the SHR model group is obviously reduced, the body weight of the SHR model group is reduced, and the SHR model group has remarkable difference ($P<0.05$ or $P<0.01$) compared with the normal control group; for high-dose groups of the ginkgolide B and derivatives thereof, the food intake and body weight of the SHR rats can be remarkably increased, and the high-dose groups have remarkable difference ($P<0.05$ or $P<0.01$) from the SHR model control group; and results are shown in table 2 and table 3.

TABLE 2

Influence on weekly food intake of SHR rats

| Group | Week | | | | | | | | |
|---|---|---|---|---|---|---|---|---|---|
| | 0 | 1 | 2 | 3 | 4 | 5 | 6 | 7 | 8 |
| | Average dairy food intake g/d | | | | | | | | |
| Normal control group | 18.5 | 19.3 | 20.4 | 21.0 | 21.5 | 23.2 | 25.0 | 26.7 | 28.1 |
| Model control group | 18.2 | 16.5* | 16.3* | 16.6** | 16.9** | 17.4** | 19.6** | 21.2** | 22.0** |
| Positive control group | 18.4 | 20.0▲ | 19.1▲ | 19.5▲ | 19.9▲ | 21.4▲▲ | 23.8▲▲ | 24.6▲▲ | 26.3▲▲ |
| GB high-dose group | 18.3 | 20.6▲▲ | 19.5▲ | 20.6▲▲ | 21.4▲▲ | 22.8▲▲ | 24.6▲▲ | 26.8▲▲ | 28.2▲▲ |
| GB low-dose group | 18.6 | 20.1▲ | 18.9▲ | 17.7 | 18.6▲ | 21.7▲▲ | 23.5▲▲ | 24.2▲▲ | 25.4▲▲ |
| BA high-dose group | 18.1 | 19.8▲ | 20.1▲▲ | 20.8▲▲ | 21.6▲▲ | 23.0▲▲ | 24.5▲▲ | 25.9▲▲ | 27.8▲▲ |
| BA low-dose group | 17.9 | 18.6▲ | 19.8▲ | 19.6▲ | 18.9▲ | 20.7▲▲ | 22.3▲▲ | 24.6▲▲ | 25.5▲▲ |
| BD high-dose group | 18.3 | 20.1▲ | 20.6▲▲ | 21.0▲▲ | 21.5▲▲ | 22.8▲▲ | 23.9▲▲ | 25.4▲▲ | 26.9▲▲ |
| BD low-dose group | 18.7 | 19.0▲ | 19.4▲ | 19.8▲ | 20.0▲▲ | 21.3▲▲ | 22.6▲▲ | 24.3▲▲ | 25.0▲▲ |
| BZ high-dose group | 18.0 | 19.3▲ | 20.5▲▲ | 22.0▲▲ | 22.6▲▲ | 23.6▲▲ | 24.1▲▲ | 24.9▲▲ | 27.0▲▲ |
| BZ low-dose group | 18.1 | 19.5▲ | 19.7▲ | 20.4▲▲ | 20.9▲▲ | 21.7▲▲ | 22.9▲▲ | 24.0▲▲ | 24.9▲▲ |
| BL high-dose group | 18.6 | 20.0▲ | 20.8▲▲ | 21.9▲▲ | 22.7▲▲ | 23.5▲▲ | 24.6▲▲ | 25.1▲▲ | 26.7▲▲ |
| BL low-dose group | 18.4 | 19.4▲ | 20.5▲▲ | 21.0▲▲ | 20.9▲▲ | 21.9▲▲ | 23.5▲▲ | 24.5▲▲ | 25.1▲▲ |
| BM high-dose group | 18.5 | 19.9▲ | 20.7▲▲ | 22.6▲▲ | 22.9▲▲ | 23.7▲▲ | 24.4▲▲ | 25.8▲▲ | 27.6▲▲ |
| BM low-dose group | 18.2 | 19.1▲ | 19.9▲ | 20.9▲▲ | 21.3▲▲ | 22.4▲▲ | 23.1▲▲ | 24.7▲▲ | 25.5▲▲ |

Note:
comparing the model control group with the normal control group, *P < 0.05, **P < 0.01; and
Comparing each drug group with the model control group, ▲P < 0.05, ▲▲P < 0.01.

TABLE 3

Influence on weekly body weight of SHR rats

| Group | Week | | | | | | | | |
|---|---|---|---|---|---|---|---|---|---|
| | 0 | 1 | 2 | 3 | 4 | 5 | 6 | 7 | 8 |
| | Body weight g | | | | | | | | |
| Normal control group | 231.2 | 250.3 | 261.5 | 285.6 | 295.4 | 310.7 | 331.6 | 345.4 | 361.7 |
| Model control group | 232.4 | 235.7* | 240.6* | 250.8** | 255.7** | 260.4** | 265.7** | 271.5** | 275.6** |
| Positive control group | 230.5 | 235.1 | 245.4▲ | 255.9▲▲ | 260.5▲▲ | 266.3▲▲ | 271.0▲▲ | 280.6▲▲ | 290.7▲▲ |
| GB high-dose group | 231.0 | 250.3▲▲ | 258.7▲▲ | 263.4▲▲ | 270.6▲▲ | 281.5▲▲ | 290.6▲▲ | 306.7▲▲ | 321.2▲▲ |
| GB low-dose group | 230.8 | 235.6 | 243.1▲ | 250.2 | 258.9▲ | 262.4 | 268.7▲ | 280.6▲▲ | 290.1▲▲ |
| BA high-dose group | 231.6 | 251.4▲▲ | 257.6▲▲ | 264.1▲▲ | 271.2▲▲ | 280.6▲▲ | 291.2▲▲ | 305.9▲▲ | 320.4▲▲ |
| BA low-dose group | 228.5 | 233.6 | 244.8▲ | 251.4 | 257.3 | 263.7▲ | 269.6▲ | 281.8▲▲ | 292.8▲▲ |
| BD high-dose group | 230.9 | 252.0▲▲ | 257.5▲▲ | 263.9▲▲ | 270.8▲▲ | 281.2▲▲ | 291.0▲▲ | 304.7▲▲ | 321.7▲▲ |
| BD low-dose group | 229.2 | 234.5 | 247.1▲▲ | 252.2 | 257.2 | 262.4 | 270.4▲ | 280.2▲▲ | 290.5▲▲ |
| BZ high-dose group | 268.9 | 249.4▲▲ | 256.7▲▲ | 262.4▲▲ | 268.9▲▲ | 280.7▲▲ | 291.3▲▲ | 305.4▲▲ | 320.9▲▲ |
| BZ low-dose group | 231.0 | 235.7 | 242.5 | 251.6 | 259.4▲ | 263.6▲ | 269.1▲▲ | 276.8▲▲ | 288.0▲▲ |

TABLE 3-continued

Influence on weekly body weight of SHR rats

| Group | Week | | | | | | | | |
|---|---|---|---|---|---|---|---|---|---|
| | 0 | 1 | 2 | 3 | 4 | 5 | 6 | 7 | 8 |
| | | | | | Body weight g | | | | |
| BL high-dose group | 230.6 | 251.8▲▲ | 257.3▲▲ | 264.1▲▲ | 270.5▲▲ | 281.7▲▲ | 290.3▲▲ | 302.8▲▲ | 315.2▲▲ |
| BL low-dose group | 230.9 | 236.4 | 243.1 | 252.8 | 260.9▲▲ | 265.8▲▲ | 270.6▲ | 277.3▲▲ | 285.4▲▲ |
| BM high-dose group | 233.4 | 249.5▲▲ | 256.8▲▲ | 264.3▲▲ | 271.6▲▲ | 280.4▲▲ | 290.5▲▲ | 305.7▲▲ | 315.8▲▲ |
| BM low-dose group | 231.5 | 236.8 | 245.7▲▲ | 253.4 | 258.3 | 263.5▲ | 271.3▲▲ | 281.6▲▲ | 292.5▲▲ |

Note:
comparing the model control group with the normal control group, *P < 0.05, **P < 0.01; and
Comparing each drug group with the model control group, ▲P < 0.05, ▲▲P < 0.01.

3.2 Pressure Lowering Effect on Spontaneously Hypertensive Rats 3.2.1 Influence on Caudal Artery Systolic Pressure of Spontaneously Hypertensive Rats Caused by Single Administration A test result shows that the caudal artery pressure of the spontaneously hypertensive rats is obviously higher than that of the normal control group and has high-remarkable difference (P<0.01) from that of the normal control group; 30 min after single administration in each drug group, an obvious pressure lowering action on the spontaneously hypertensive rats is achieved, the systolic pressure has an obvious lowering trend at each time point after administration and has remarkable difference (P<0.05 or P<0.01) from that of the SHR model group, the pressure lowering action can be continued to 120 min after administration, and the blood pressure also has remarkable difference (P<0.05 or P<0.01) at 30 min, 60 min, 90 min and 120 min after administration compared with that before administration, referring to table 4.

TABLE 4

Influence on caudal artery systolic pressure of spontaneously hypertensive rats caused by single medication in each drug group (x ± s, n = 8)

| Group | Systolic pressure/mmHg (1 mmHg = 0.133322 kPa) | | | | |
|---|---|---|---|---|---|
| | Before administration | 30 min | 60 min | 90 min | 120 min |
| Normal control group | 125.32 ± 4.65 | 126.44 ± 4.52 | 125.74 ± 4.89 | 124.65 ± 5.81 | 125.30 ± 5.25 |
| Model control group | 165.31 ± 6.78** | 163.56 ± 5.65** | 163.23 ± 6.34** | 164.69 ± 6.75** | 164.28 ± 4.86** |
| Positive control group | 161.24 ± 11.03 | 149.75 ± 8.09▲▲# | 140.95 ± 9.50▲▲## | 139.23 ± 6.04▲▲## | 134.41 ± 8.31▲▲## |
| GB high-dose group | 167.49 ± 13.09 | 151.46 ± 16.27▲# | 157.54 ± 17.95 | 160.26 ± 16.54 | 152.21 ± 18.27▲# |
| GB low-dose group | 168.41 ± 12.30 | 160.42 ± 9.56 | 153.15 ± 12.51▲# | 155.16 ± 11.26# | 159.17 ± 11.63 |
| BA high-dose group | 163.64 ± 10.31 | 149.69 ± 11.62▲▲# | 155.68 ± 17.35 | 161.30 ± 15.64 | 158.25 ± 15.61 |
| BA low-dose group | 165.35 ± 11.62 | 161.36 ± 9.52 | 159.62 ± 14.25 | 152.56 ± 11.26▲# | 159.87 ± 11.32 |
| BD high-dose group | 164.57 ± 13.25 | 148.47 ± 10.87▲▲## | 151.75 ± 10.68▲# | 157.25 ± 14.38 | 160.49 ± 14.76 |
| BD low-dose group | 163.64 ± 14.02 | 157.74 ± 9.28 | 152.67 ± 13.52▲# | 151.60 ± 12.04▲# | 155.68 ± 10.15 |
| BZ high-dose group | 166.24 ± 12.14 | 150.00 ± 9.15▲▲## | 152.95 ± 9.26▲# | 156.28 ± 13.95 | 169.36 ± 10.63 |
| BZ low-dose group | 163.58 ± 10.36 | 152.65 ± 10.48▲# | 153.05 ± 16.39 | 151.14 ± 10.87▲# | 156.47 ± 12.47 |
| BL high-dose group | 164.25 ± 11.69 | 148.01 ± 5.98▲▲## | 151.36 ± 9.45▲# | 152.95 ± 12.54▲# | 151.98 ± 9.26▲# |
| BL low-dose group | 165.68 ± 16.35 | 158.36 ± 10.54 | 154.68 ± 12.48 | 152.74 ± 12.58▲# | 152.04 ± 10.02▲# |
| BM high-dose group | 163.45 ± 15.24 | 149.04 ± 10.95▲▲## | 151.58 ± 9.85▲# | 153.65 ± 11.04▲# | 151.00 ± 9.85▲# |
| BM low-dose group | 166.27 ± 14.01 | 156.21 ± 9.68 | 152.06 ± 9.78▲# | 151.74 ± 13.15▲# | 152.52 ± 15.06▲# |

Note:
comparing the model control group with the normal control group, **P < 0.01;
comparing each drug group with the model control group, ▲P < 0.05, ▲▲P < 0.01; and compared with pre-administration, #P < 0.05, ##P < 0.01.

3.2.2 Influence on Caudal Artery Systolic Pressure of Spontaneously Hypertensive Rats Caused by Continuous Administration A test result shows that the blood pressure of spontaneously hypertensive rats gradually rises along with increase of age and has high-remarkable difference (P<0.01) compared with that of the normal control group, and from 7th day to 56th day of the test, the blood pressure has remarkable difference (P<0.05 or P<0.01) compared with that before the test; each drug group can remarkably inhibit a pathological progress of blood pressure rise of the spontaneously hypertensive rats, both the systolic pressure and diastolic pressure are lowered to some extent at different time periods after continuous medication, pressure lowering processes of low-dose groups of all the drug groups present certain fluctuation, pressure lowering processes of high-dose groups present a relatively stable pressure lowering effect, and the pressure lowering processes have remarkable difference (P<0.05 or P<0.01) compared with that of a model group and before medication, referring to table 5.

TABLE 5

Influence on caudal artery systolic pressure of spontaneously hypertensive rats caused by 8 weeks of continuous medication in each drug group (x ± s, n = 8)

| Group | Systolic pressure/mmHg (1 mmHg = 0.133322 kPa) | | | | |
|---|---|---|---|---|---|
| | Before administration | 1 d | 7 d | 13 d | 19 d |
| Normal control group | 125.32 ± 4.65 | 126.30 ± 5.10 | 124.28 ± 4.78 | 125.97 ± 6.54 | 125.77 ± 5.85 |
| Model control group | 165.31 ± 6.78** | 164.85 ± 6.24** | 165.95 ± 5.37** | 164.88 ± 8.24** | 163.71 ± 7.19** |
| Positive control group | 161.24 ± 11.03 | 145.17 ± 6.42▲▲# | 142.05 ± 7.24▲▲## | 140.36 ± 9.20▲▲## | 138.39 ± 7.26▲▲## |
| GB high-dose group | 167.49 ± 13.09 | 150.63 ± 10.25▲# | 148.54 ± 9.27▲# | 141.74 ± 8.26▲▲## | 140.95 ± 12.04▲▲## |
| GB low-dose group | 168.41 ± 12.30 | 155.67 ± 12.36# | 153.46 ± 10.74▲# | 156.25 ± 10.84 | 150.68 ± 9.78▲# |
| BA high-dose group | 163.64 ± 10.31 | 151.48 ± 9.85▲# | 150.95 ± 9.68▲# | 145.30 ± 11.62▲▲## | 142.39 ± 12.49▲▲## |
| BA low-dose group | 165.35 ± 11.62 | 155.29 ± 10.98# | 158.73 ± 13.82 | 153.64 ± 9.75▲# | 154.85 ± 9.74# |
| BD high-dose group | 164.57 ± 13.25 | 150.49 ± 15.34▲# | 152.64 ± 11.45▲# | 147.33 ± 13.42▲▲## | 145.49 ± 12.98▲▲## |
| BD low-dose group | 163.64 ± 14.02 | 156.20 ± 13.41 | 152.95 ± 11.03▲# | 155.74 ± 15.25 | 153.01 ± 14.04▲# |
| BZ high-dose group | 166.24 ± 12.14 | 154.69 ± 9.85▲# | 153.74 ± 10.24▲# | 150.39 ± 10.39▲# | 149.72 ± 9.83▲▲## |
| BZ low-dose group | 163.58 ± 10.36 | 158.77 ± 11.06 | 153.41 ± 14.08▲# | 151.38 ± 9.47▲# | 155.74 ± 10.62 |
| BL high-dose group | 164.25 ± 11.69 | 153.56 ± 8.15▲# | 152.74 ± 10.25▲# | 149.52 ± 10.24▲▲## | 149.05 ± 11.09▲▲## |
| BL low-dose group | 165.68 ± 16.35 | 154.08 ± 11.54▲# | 156.92 ± 9.82 | 156.07 ± 8.52 | 153.96 ± 11.07▲# |
| BM high-dose group | 163.45 ± 15.24 | 154.62 ± 5.74 | 152.31 ± 10.56▲# | 151.58 ± 12.06▲# | 153.06 ± 10.41▲# |
| BM low-dose group | 166.27 ± 14.01 | 155.25 ± 12.36# | 154.85 ± 10.49▲# | 153.26 ± 12.95▲# | 156.74 ± 10.36 |

| Group | Systolic pressure/mmHg (1 mmHg = 0.133322 kPa) | | | |
|---|---|---|---|---|
| | 25 d | 35 d | 49 d | 56 d |
| Normal control group | 125.41 ± 6.27 | 126.17 ± 5.70 | 124.25 ± 8.14 | 126.14 ± 7.59 |
| Model control group | 164.76 ± 8.04** | 165.26 ± 7.35** | 164.96 ± 7.28** | 164.37 ± 8.92** |
| Positive control group | 145.02 ± 7.30▲▲# | 139.08 ± 6.72▲▲## | 135.47 ± 8.47▲▲## | 130.39 ± 4.65▲▲## |
| GB high-dose group | 147.46 ± 9.85▲▲# | 142.33 ± 10.38▲▲## | 138.79 ± 11.58▲▲## | 135.28 ± 7.48▲▲## |
| GB low-dose group | 155.65 ± 10.57# | 154.25 ± 10.74▲# | 150.56 ± 10.42▲## | 153.85 ± 9.24▲# |
| BA high-dose group | 145.84 ± 11.46▲# | 143.67 ± 115.62▲▲## | 140.69 ± 14.72▲▲## | 139.88 ± 13.04▲▲## |
| BA low-dose group | 151.36 ± 10.58▲# | 153.72 ± 13.68▲# | 151.70 ± 13.10▲# | 153.72 ± 12.54▲# |
| BD high-dose group | 147.66 ± 14.02▲▲## | 145.61 ± 9.47▲▲## | 148.62 ± 12.04▲▲## | 142.15 ± 13.14▲▲## |
| BD low-dose group | 152.30 ± 10.45▲# | 157.03 ± 14.08 | 153.96 ± 14.74▲# | 154.57 ± 12.48▲# |
| BZ high-dose group | 149.02 ± 8.26▲▲## | 151.72 ± 10.47▲# | 153.42 ± 12.04▲# | 148.62 ± 9.73▲▲## |
| BZ low-dose group | 154.94 ± 9.64▲# | 150.95 ± 5.04▲# | 155.06 ± 6.37 | 153.95 ± 14.01▲# |
| BL high-dose group | 147.09 ± 12.68▲▲## | 147.52 ± 10.64▲▲## | 150.94 ± 11.06▲# | 149.76 ± 12.63▲▲## |

TABLE 5-continued

Influence on caudal artery systolic pressure of spontaneously hypertensive rats caused by 8 weeks of continuous medication in each drug group (x ± s, n = 8)

| | | | | |
|---|---|---|---|---|
| BL low-dose group | 154.57 ± 9.74▲# | 153.67 ± 11.58▲# | 149.68 ± 10.42▲▲## | 153.62 ± 9.47▲# |
| BM high-dose group | 148.54 ± 11.62▲▲## | 149.36 ± 10.75▲▲## | 150.32 ± 9.59▲# | 149.78 ± 11.64▲▲## |
| BM low-dose group | 154.75 ± 10.39▲# | 151.48 ± 10.32▲# | 151.17 ± 14.05▲# | 154.64 ± 11.42▲# |

Note:
comparing the model control group with the normal control group, **P < 0.01;
comparing each drug group with the model control group, ▲P < 0.05, ▲▲P < 0.01; and compared with pre-administration, #P < 0.05, ##P < 0.01.

The above-mentioned test data show that high-dose groups and low-dose groups of the ginkgolide B derivative and the ginkgolide B can be used for remarkably lowering the blood pressure value of the spontaneously hypertensive rats after single and continuous administration, and thus, the ginkgolide B derivative and the ginkgolide B have a remarkable pressure lowering action.

In summary, the ginkgolide B derivative and salt thereof, provided by the present invention, have obvious improved water solubility compared with that of ginkgolide B, and thus, the defects of the ginkgolide B that the water solubility is poor, the bioavailability is low, and the drug effect cannot be brought into full play are excellently overcome. A drug effect test shows that the compound provided by the present invention has a remarkable therapeutic action on cardiovascular and cerebrovascular diseases and can be applied to the prevention and/or hypertension, cerebral apoplexy, coronary diseases, arrhythmia, heart failure, dyslipidemia, pulmonary vascular diseases, chronic kidney diseases and peripheral vascular diseases, etc., such as myocardial infarction, coronary artery diseases, atherosclerosis, left main diseases, bifurcation lesions, angina pectoris, thrombosis, pulmonary heart diseases, endocrinopathy heart diseases, anemic heart diseases, cardiac neurosis, nutritional metabolic heart diseases, aortic aneurysm, lower extremity atherosclerotic diseases, peripheral arterial diseases, intracranial aneurysm, arteriosclerotic aneurysm, ischemic cerebral apoplexy, hemorrhagic cerebral apoplexy, hyperlipidemia, arteriosclerosis, exercise-related sudden death, sudden cardiac death, apoplexy, hypotension, vascular thrombosis, pulmonary embolism, atrial fibrillation, hypertensive encephalopathy, hypertension with cerebral stroke, cerebral hemorrhage, cerebral thrombosis, cerebral embolism, cerebral infarction, cerebral arteritis, cerebral arteriosclerosis, lacunar infarction, vascular dementia, chronic kidney diseases, chronic cardiac insufficiency, gouty nephropathy, diabetic nephropathy and/or abnormal renal function, and thus, a new choice is provided for clinically preventing and/or treating the cardiovascular and cerebrovascular diseases.

The invention claimed is:

1. A compound as shown in formula IIb or a pharmaceutically acceptable salt thereof:

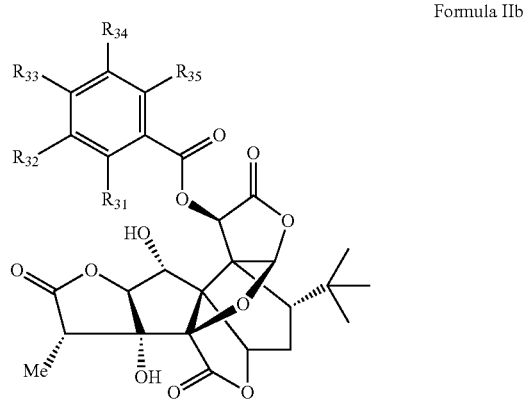

Formula IIb wherein $R_{32}$, $R_{33}$, $R_{34}$ and $R_{35}$ are H simultaneously; and wherein $R_{31}$ is selected from a $C_2$-$C_6$ ester group or ester group substituted alkyl as shown in formula A:

Formula A wherein $R_{311}$ and $R_{312}$ are separately or simultaneously selected from $C_2$-$C_6$ ester group or $C_1$-$C_6$ alkyl, and $R_{311}$ and $R_{312}$ are not $C_1$-$C_6$ alkyl simultaneously.

2. The compound or pharmaceutically acceptable salt thereof according to claim 1, characterized in that the pharmaceutically acceptable salt is selected from organic acid salts or inorganic acid salts.

3. A pharmaceutical composition, comprising the compound or pharmaceutically acceptable salt thereof according to claim 1 as an active ingredient, and comprising pharmaceutically acceptable accessories or auxiliary ingredients.

4. A pharmaceutical composition, comprising the compound or pharmaceutically acceptable salt thereof according to claim 2 as an active ingredient, and comprising pharmaceutically acceptable accessories or auxiliary ingredients.

* * * * *